United States Patent [19]

Elbert et al.

[11] Patent Number: 4,801,187
[45] Date of Patent: Jan. 31, 1989

[54] LIQUID LIGHT TUBE END CAP ASSEMBLY

[75] Inventors: Lawrence E. Elbert, Huntington Beach; John C. Mazza, El Toro; Raymond L. Hecker, Mission Viejo, all of Calif.

[73] Assignee: Baxter Travenol Laboratories, Inc., Deerfield, Ill.

[21] Appl. No.: 858,218

[22] Filed: Apr. 30, 1986

[51] Int. Cl.⁴ .................................................. G02B 6/26
[52] U.S. Cl. .............................. 350/96.15; 350/96.10; 350/96.20; 350/96.29; 350/96.32
[58] Field of Search ............... 350/96.10, 96.20, 96.24, 350/96.29, 96.30, 96.32, 96.15

[56] References Cited

U.S. PATENT DOCUMENTS

| | | | |
|---|---|---|---|
| 3,740,113 | 6/1973 | Cass | 350/96.10 |
| 3,906,221 | 9/1975 | Mercier | 350/96.10 X |
| 4,045,119 | 8/1977 | Eastgate | 350/96.15 |
| 4,458,983 | 7/1984 | Roberts | 350/96.20 |
| 4,577,110 | 3/1986 | MacBride et al. | 250/461.2 |
| 4,669,818 | 6/1987 | Myer | 350/96.20 |

OTHER PUBLICATIONS

Brochure entitled "This is Paramax" by American Dade a division of American Hospital Supply Corporation.

*Primary Examiner*—John D. Lee
*Assistant Examiner*—Phan T. Heartney
*Attorney, Agent, or Firm*—Marjorie D. Hunter; Susan Fentress; Paul C. Flattery

[57] ABSTRACT

An improved and unique liquid light tube (guide) end cap assembly particularly useful in a system for the clinical analysis of liquid biological samples for directing wavelengths of light is described. The assembly comprises a light guide having projecting at one end portion thereof a quartz member and a housing for containing the end portion of the light guide and the quartz member, thereby forming an aperture between the quartz member and the housing, the aperture having a depth of between about 0.002 and 0.007 inches.

13 Claims, 4 Drawing Sheets

LIQUID LIGHT TUBE END CAP ASSEMBLY

BACKGROUND OF THE INVENTION

I. Field of the Invention

This invention relates generally to the analysis of materials, and more particularly to a new arrangement for the end portion of a light guide which directs light to to photospectormeter from a liquid sample located in a cuvette. The present invention is particularly useful in automated chemistry analyzers which are employed for determining the presence and levels of one or more selected constituents in relatively small biological liquid samples.

II. Description of the Prior Art

Numerous automated clinical analyzers are known and widely used in hospital clinical laboratories. An example of such an analyzer is the multi-channel type analyzer.

A multi-channel analyzer is one in which a series of different tests are performed simulataneously by the analyzer, and in parallel with one another. Such an analyzer can be best visualized as a series of batch analyzers operating in parallel wherein each channel performs a single analysis test. The multi-channel type analyzer generally utilizes a liquid reagent to react with the particular constituent being tested in the sample and a photo-optical system to read the optical absorbence of the sample which corresponds to the level of the constituent in the sample.

Although this type of automated analyzer has received wide acceptance in the clinical laboratory, certain drawbacks are associated with its use. For example, although the multi-channel type analyzer is reliable due to its simplicity, cost effective for large number of samples and has a relatively high test throughout rate, it is limited in the sense that it can only be effectively utilized to perform a single constituent analysis at a time on a relatively large number of samples. In addition, such analyzers are not capable of performing emergency "stat" tests due to their relatively long and complex set up time and their inherent inability to economically analyze a single test sample. Thus, the efficiency of this type of system is not the best.

A further significant disadvantage found is that although tests can be simultaneously performed for multiple constituents on the same sample, generally all of these tests must be performed for every sample whether desired or not. This results in waste of both sample material and the reagents used in the unnecessary tests. Furthermore, due to the fact that multiple discrete and dedicated channels are utilized in such an instrument, there is significant duplication of numerous components which adds to the complexity and expense of the overall instrument.

An automated single track clinical analyzer which avoids the above-described drawbacks is described in commonly owned U.S. Pat. No. 4,528,157 entitled, "Automated Analysis Instrument System", the disclosure of which is hereby incorporated by reference in its entirety. Furthermore, by using a unique photo-optical system, described in commonly owned U.S. Pat. No. 4,528,159 entitled, "Multichannel Spectrophotometer", the disclosure of which is hereby incorporated by reference in its entirety, greater flexibility of analysis at each analysis station is achieved. This is because this photo-optical system employs fiber optic bundles or similar light guides to transmit variable wavelengths of light to each analysis station from a single light source.

The single track analyzer utilizes a disposable cuvette belt formed from thin plastic film defining a series of discrete reaction compartments (cuvettes) which are transported in line through the instrument. Such a cuvette belt is described in commonly owned, abandoned U.S. patent application Ser. No. 284,842, filed July 20, 1981 entitled, "Cuvette System for Automated Chemical Analyzers". This belt provides hanbling flexibility and avoids the cross-contamination associated with flow-through cuvettes as well as avoiding the washing required for reusable cuvettes.

In employing a photo-optical system for critical analysis work, it is very important that there be substantially no interference with the path of light that is directed from the sample being analyzed through a light tube which in turn directs the light to a photospectrometer. Any interference with this light path can effect the accuracy of the analysis, and lead to incorrect results. However, it is typical of many of the prior art analysis systems that a good deal of "noise" is received from the light signal sent to a photospectrometer from a sample being analyzed. This noise causes a scattering of the test results. Also, the test results tend to "float". When using a series of photospectrometers in an analysis system there is a tendency to avoid focussing of the light signal to the photospectrometers thereby introducing tracing errors from one analyzer to another analyzer. The end result of all of these problems is that the level of accuracy of the analysis is reduced.

SUMMARY OF THE INVENTION

It is therefore an object of the present invention to overcome the disadvantages of many of the analysis systems employing photo-optical systems as disclsed by the prior art.

It is an object of the present invention to provide a photo-optical analysis system that employs unique light guides to transmit various wavelengths of light to each analysis station from a single light source. It is to be noted that the term "light" as used herein should be considered in its broadest sense to include both visible wavelengths and non-visible spectral analysis wavelengths.

It is a further object of the present invention to provide a photo-optical analysis system that employs a unique structure for the systems light tube which substantially improves both the precision of the readings being obtained and the accuracy of the analysis being sought.

It is a further object of the present invention to provide a photo-optical analysis system that employs a unique structure for the systems light tube that prevents any scratching or abrasion of the light tube by a passing cuvette in which the sample being analyzed is contained.

It is still a further object of the present invention to provide a photo-optical analysis system that employs a unique structure for the systems light tube that prevents interference with the path of light from the sample being analyzed to the photospectrometer by shortening the amount (distance) of bath water that the light passes through in traveling from the sample being analyzed to the light tube. This substantially prevents the formation of bubbles or lodging of debris in the open space area between the light tube and the cuvette containing the sample.

The foregoing objects and others are accomplished in accordance with the present invention by providing an automated instrument system for analyzing the constituents of a specimen sample wherein the sample is contained in a cuvette and light is directed to the sample, into a light guide and to a photo-optical system for analyzing the sample, the system employing an improved light guide assembly. The improved light guide assembly comprises a light guide having projecting at one end portion thereof a quartz member and a housing for containing the end portion of the light guide and the quartz member. The critical improvement of this invention (which includes a light guide assembly as described herein that can be used in an automated instrument system for analysis and which avoids the disadvantages outlined above) lies in forming an aperture between the quartz member and the housing, the aperture having a depth of about 0.002 to 0.007 inches.

BRIEF DESCRIPTION OF THE DRAWINGS

For a better understanding of the invention as well as other objects and further features thereof, reference is made to the following detailed disclosure of this invention taken in conjunction with the accompanying drawings wherein.

DESCRIPTION OF THE PREFERRED EMBODIMENTS

Figure 1:
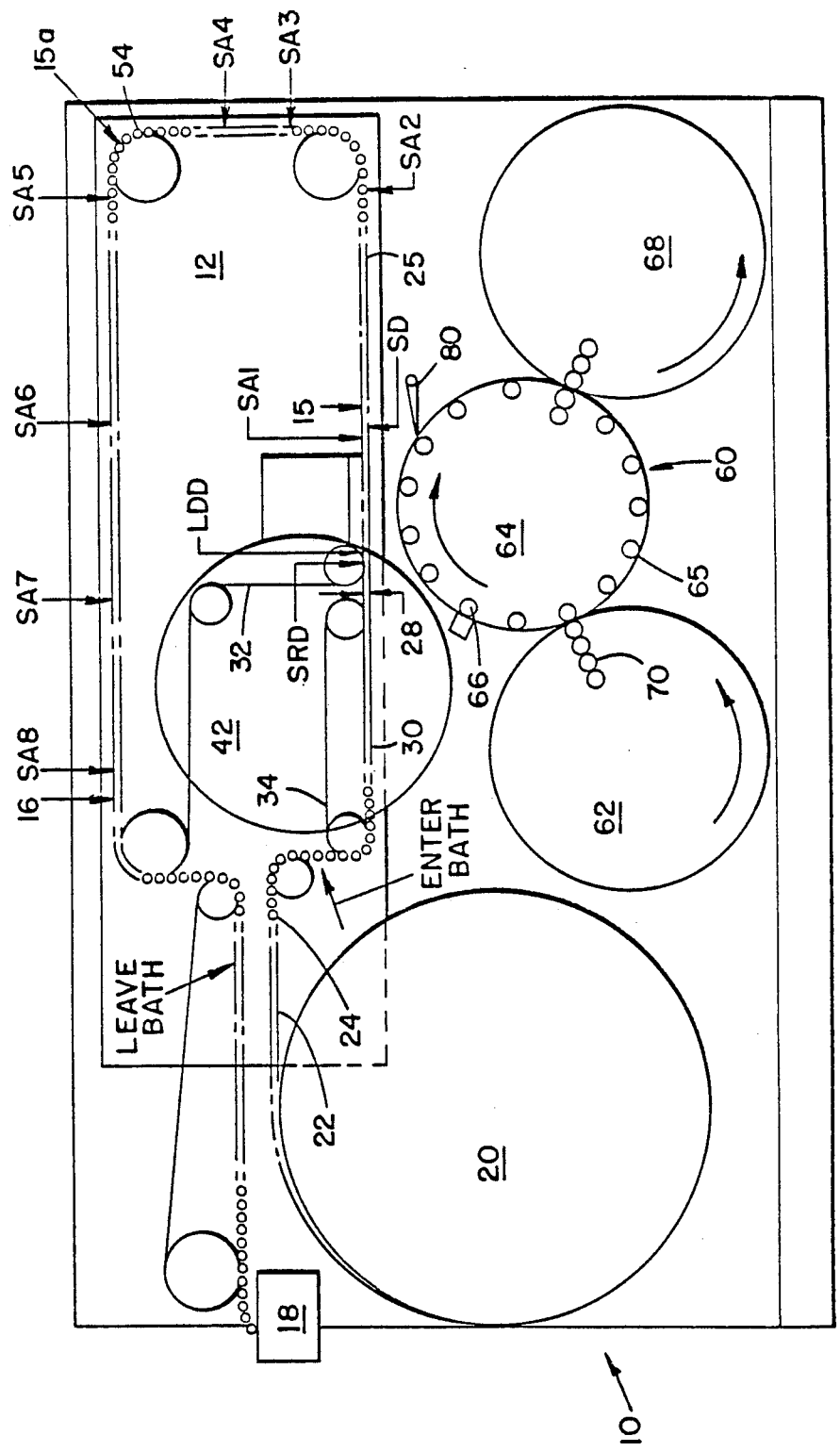
FIG. 1 is a schematic plan view of an automated clinical analyzer that can incorporate the features of the present invention.
Figure 2:
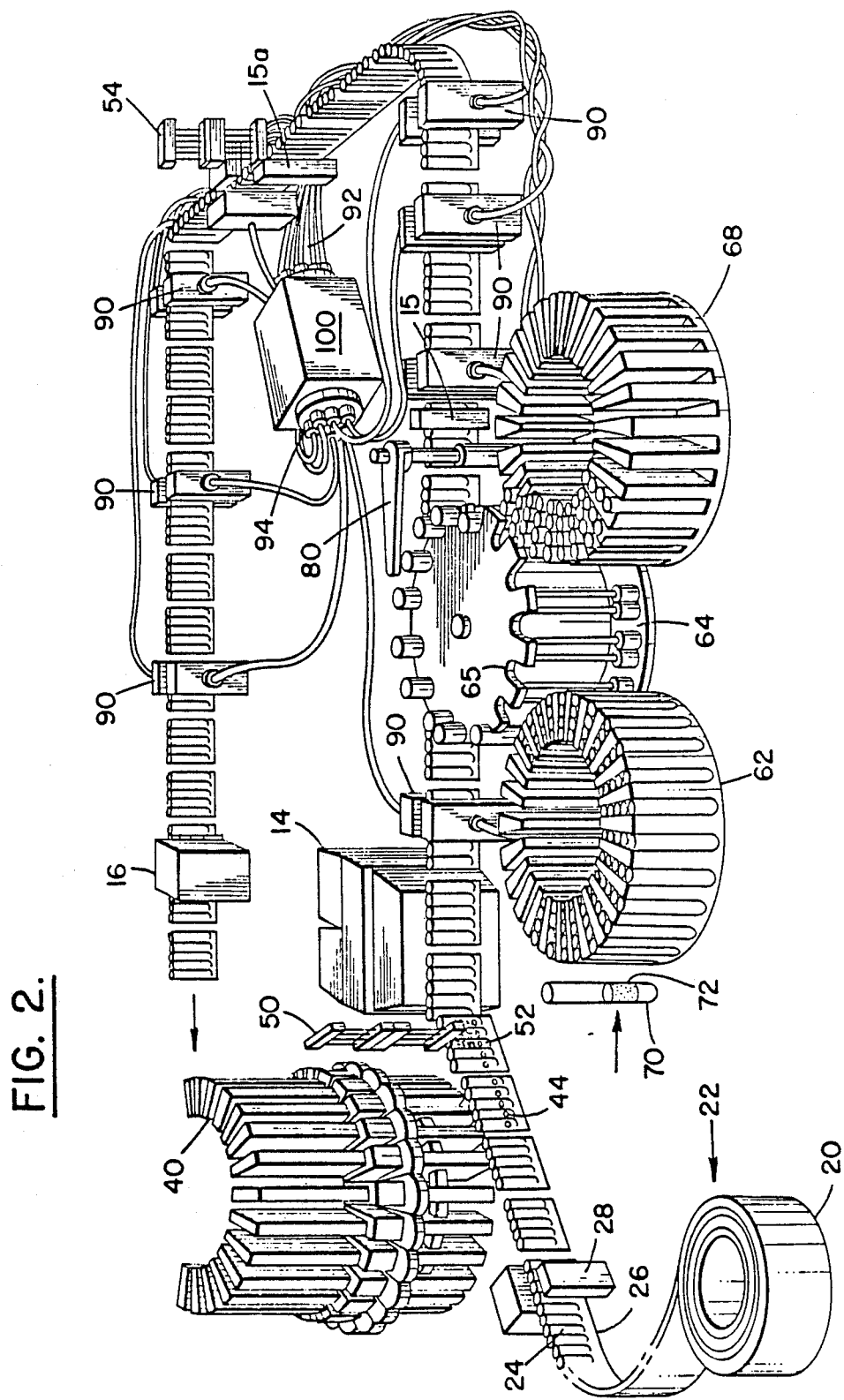
FIG. 2 is a partical perspective view of the automated clincial analyzer shown in FIG. 1.

FIGS. 1 and 2 illustrate as one example, an automated clincial analyzer 10 as generally described in commonly owned U.S. patent application Ser. No. 848,851, a continuation of Ser. No. 575,924, filed Feb. 1. 1984, now abandoned and entitled "Clinical Analysis Systems and Methods", that can incorporate the features of the present invention. More particularly, the analyzer is Paramax Analytical System as manufactured by Baxter Health Care Corporation. The analyzer 10 is particularly adapted for the testing of constituents in biological fluids, such as blood samples.

The analyzer comprises a series of processing stations past which strips of disposable reaction cuvettes are indexed or advanced. The cuvettes 24 are supplied from a supply reel 20 as a continuous cuvette belt 22 and are indexed through the analyzer by tractor conveyor 30 which engages a row of index holes in the cuvette belt. The cuvettes are indexed in turn past the following stations: a belt cutter 28 for dividing the belt into sections; a tabletted reagent dispenser 40; a diluent and liquid reagent dispenser 50; an ultrasonic mixing horn 14; a sample dispenser 80 for dispensing biological samples delivered by a transfer carousel 64; an air jet mixing apparatus 15 including an apparatus for squeezing the top (opening) of the cuvette during the air jet mixing process as described in commonly owned U.S. patent application Ser. No. 858,366, filed Apr. 30, 1986 entitled, "Improved Clinical Analysis Methods and Systems"; eight photometric read stations 90; a further reagent dispenser 54; a further air jet mixing apparatus 15a for mixing the sample and the further reagent; a cuvette sealer 16 and a cuvette collection station 18. During their passage through the analyzer, the cuvettes are carried in a water bath 12 maintained at a constant temperature.

Figure 3:
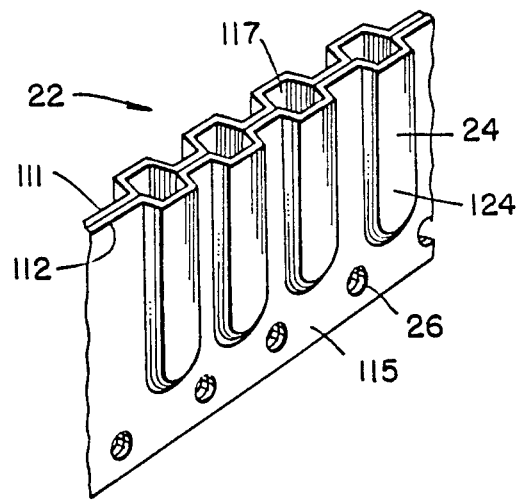
FIG. 3 is a perspective view of a cuvette belt for use in the clinical analyzer of FIG. 1 and 2.

The cuvette belt 22 is preferably constructed and made in the manner more fully described in the aforesaid U.S. patent application Ser. No. 284,842. As shown in FIG. 3, the belt 22 comprises two strips 111, 112 of transparent flexible plastic material which are moulded and sealed together to form a series of discrete, side-by-side parallel compartments (cuvettes) 24 separated by webs 115. The compartments are closed at one end and have a top or opening or open mouth 117 at the other end so as to receive and retain fluid therein. For example, the cuvettes can be in the order of size so as to be capable of holding about 500 microliters of fluid. The flat web material 115 between the vessels 24 includes a transport strip portion extending alongside the closed ends thereof which is formed with indexing perforations or holes 26. These perforations are engaged by the tractor transport 30 or the analyzer 10 for conveying the cuvettes therethrough and maintaining a precise alignment of the optical paths throug the cuvettes with the photo-optical examining system at analysis stations 90.

The transport 30 comprises a single continuous guide and support track extending through the analyzer having a main tractor belt 32 which engages the indexing holes 26 in the cuvette belt 22 and advances the cuvettes through the instrument at a predetermined rate of advance. A short loading belt 34 threads the cuvette belt 22 into engagement with the main tractor belt 32. The transport 30 advances or indexes the cuvettes through the analyzer 20 in steps corresponding to the spacing between cuvettes (the pitch of the belt) with the cuvettes being stopped and held stationary for a dwell period between each advance. Each step may suitably correspond to a time interval of 5 seconds with a 4 second dwell time between each indexing advance of the cuvettes.

The reagent tablet dispenser carousel 42 comprises a circular array of tabletted reagent dispensers 40 and can be rotated to bring the correct solid reagent dispenser to solid reagent dispensing point "SRD" to drop a single reagent tablet 44 into a cuvette 24. As illustrated, the carousel 42 accommodates thirty-two reagent tablet dispensers 40. It is rotated under microprocessor control to bring the correct tablet dispenser to the dispensing point for each cuvette. The dispensers 40 are detachable and can be loaded randomly. An automatic flagging system indicates when a dispenser is low in tablets.

The diluent and/or liquid reagent dispenser 50 is located adjacent to carousel 42 for adding sufficient diluent 52 for reagent tablet 44 dissolution and/or for dispensing a liquid reagent into the reaction vessel (cuvette) 24 at point "LDD".

The ultrasonic horn 14 acts on the cuvette contents for a sufficient length of time; for example, 45 seconds, to totally dissolve the reagent tablets.

A sample loading and transfer carousel assembly 60 is located downstream of the reagent and diluent dispensers. This carousel assembly comprises a loading carousel 62 into which patient samples 70 are randomly loaded; a transfer carousel 64 which accepts the patient samples 70 from loading carousel 62, identifies the patient sample by means of a bar code reader 66 which reads a bar code label 72 placed on the patient sample container and continuously feeds the patient samples into the system; and finally, an unloading carousel 68 receives the patient samples 70 after testing and stores them in an organized manner in the event that they must later be located and retrieved.

The loading carousel 62 permits continuous random loading of up to 96 patient samples. The transfer carousel 64 continuously feeds patient samples into the system for maximum throughput. Standard collection tubes or micro samples tubes may be accommodated thus allowing utilization of the same containers in which the sample is collected; for example, in the case of blood samples, the "Vacutainer" tube which is commonly used to draw the serum specimen.

Sample 80 for dispensing samples into the cuvettes 24 at point "SD" is located adjacent to transfer carousel 64. This sampler is designed to aspirate about 2 to 20 microliters of patient sample 70 from its container in the transfer carousel and dispense it into a cuvette 24 during the four second dwell period while the cuvette is aligned with the angler.

The air jet mixing apparatus 15 (and 15a) direct an air jet preferably at an acute angle against the liquid surface in the cuvette adjacent its junction with the cuvette wall to create a vortex thus producing a thorough mixing of the sample with the reagent and diluent in accordance with the teachings of the system as described in the aforesaid U.S. patent application Ser. No. 848,821. In a preferred embodiment, the apparatus has a fixed, inclined nozzle and the cuvettes 24 are aligned in position beneath the nozzle and the air jet is switched on only during the dwell period when the cuvette is stationery. In order to ensure that the air jet correctly strikes the liquid surface, the liquid level is closely controlled.

Figure 4:
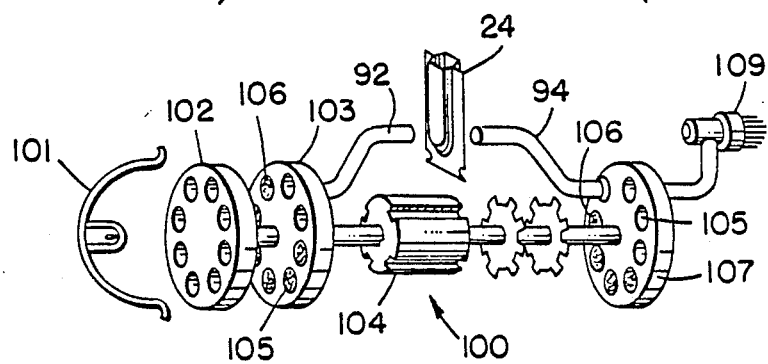
FIG. 4 is a partial schematic representation of a preferred photo-optical system utilized with the analysis system of FIGS. 1 and 2.

Eight photometric analysis stations 90 are located at points "SA1" through "SA8" along the cuvette track 30. These analysis stations are connected by individual optical guides 92 and 94 to photo-optical system 100. The station "SA1" is arranged following the ultrasonic horn 14 for verifying proper reagent dispensing and dissolution. This system is illustrated in FIG. 4.

The photo-optical system comprises a single light source 101 for generating selected wavelengths of light. The output of light source 101 is focused by fixed focusing lens 102 onto the multiple wavelength selective filters disposed about the circumference of rotary source filter wheel 103. The rotation of source filter wheel 103 is regulated by the instrument control microprocessor through double shafted motor 104. The output from source filter wheel 103 is sequentially transmitted through separate light guides 92 to each of the analysis stations.

At the analysis stations, the filtered light energy is passed through the reaction compartment 24 containing the mixture to be analyzed. The output of the analysis stations is then passed back to the photo-optical system 100 via separate light guides 94. At this point, a second filter wheel 107, which preferably is identical to and synchronized with source filter wheel 103, intercepts the outputs of light guides 94 before this output is directed to a separate photodetector tube 109 for each analysis station. A reflector may be utilized to focus the output of filter wheel 107 on photodetector tubes 109. In the representation of FIG. 4, only one set of light guides 92, 94 and one photodetector tube 109 is shown for simplicity, although it is to be understood that eight of these elements (one for each analysis station) are required.

The outputs of photodetector tubes 109 are monitored by the control microprocessor and appropriate wavelength output values for each analysis reaction at each analysis station is stored by the microprocessor. When the reaction is completed, the microprocessor will utilize this stored information to calculate the concentration of the selected sample constituent and provide this result to the instrument operator.

As can be seen from FIG. 4, each filter wheel has seven different wavelength selective filters 105 disposed about its circumference. In addition, an opaque blank 106 is located thereon in order to establish the residual "dark current" level of the electronics. Hence, great flexibility is provided by permitting any one or combination of the seven wavelengths to be read at any analysis station for any sample during the four second analysis period. In that filter wheels 103, 107 are rotated at thirty revolutions per second in the preferred embodiment, thirty readings at a particular wavelength may be made each second which can then be averaged to provide a highly accurate final value by the microprocessor.

The second reagent dispenser 54 permits further reaction of the sample to be obtained following initial testing and is shown arranged between analysis stations "SA4" and "SA5". It could be located between any of the analysis stations "SA2" to "SA8". This capacity for optional reagent additions or triggered reaction capability gives added analytical versatility for multiple reagent test situations.

The further air jet mixing apparatus 15a provides for thorough remixing of the cuvette contents following addition of further reagent at station 54.

The cuvette sealer 16 seals the tops of the tested cuvettes for convenient clean disposal of completed samples at the cuvette disposal location where they are neatly collected into a lined disposal bin.

The microprocessor control system of the clinical analyzer, which suitably has a 280 processing unit, controls all the operating units thereof in accordance with sample and test information inputted at a suitable operator interface keyboard. In accordance with the desired test results, quantities of a single sample may be dispensed into one or more cuvettes either alone or in combination with any one or more of the solid and liquid reagents and diluents, and examined at any one or more of the analysis stations 90. Test results are displayed on a screen and can be printed out.

Figure 5:
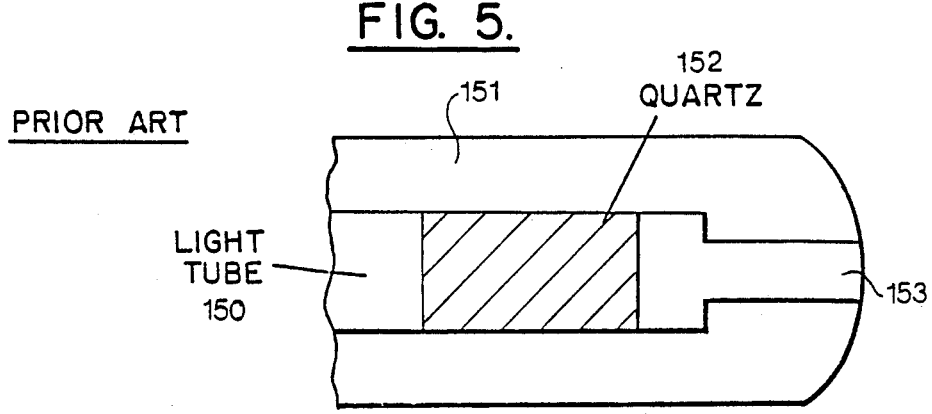
FIG. 5 is a plan view of an end portion of a light guide assembly as described in the prior art.

Turning now specifically to the unique features of the present invention, there is shown in FIGS. 5 a typical end portion of a light guide assembly as described in the prior art. In comparison there is shown in FIG. 6 an end portion of a light guide assembly in accordance with the features of the present invention suitable for use as the end portion of optical guides 92 and 94 (see FIG. 4) in the automated clinical analyzer described above at analysis station 90.

The prior art generally describes light guide assemblies for clinical analyzers that employ end caps and liquid light tubes having the basic configuration as illustrated in FIG. 5. A known assembly includes a light guide in the form of a liquid light tube 150 that is encased by a housing 151 up to the end cap area. The end cap is joined onto the liquid light tube 150 and contains a quartz member 152 and an aperture 153. Since the entire assembly is immersed in a water bath (this is typical of this type of light guide assembly when used in a clinical analyzer as described hereinabove), the water fills the aperture and space inside the end cap leading up to the end face of quartz member 152. During the analysis procedure, light is passed through a cuvette having the sample being analyzed therein, through the length of bath water in the aperture 153, into and through the quartz member 152 and into and through the light tube 150. Specifically, because of the aperture arrangement and the length (distance) the light must travel in the water to get from the sample in the cuvette to the quartz member, there is a great tendency to form bubbles and trap debris in the aperture. Both the bubbles and the debris substantially interfere with the critical accuracy of the analysis. The prior art light guide assembly introduces a good deal of noise in the signal that is received by the photospectrometer which causes scattering of the test results. Also, the test results tend to float thereby descreasing the overall accuracy of the analysis results.

Figure 6:
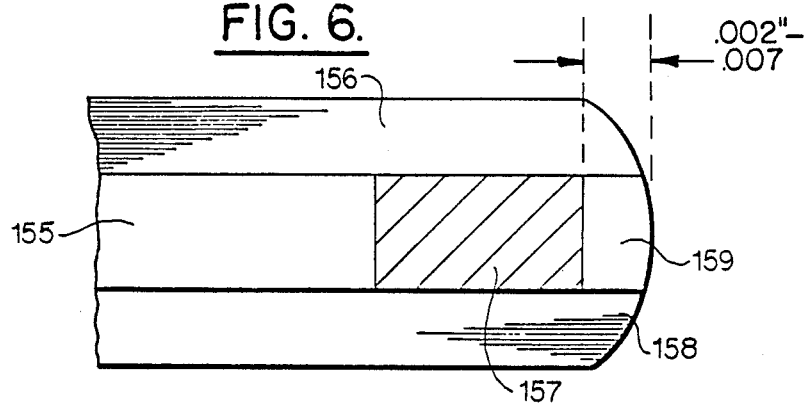
FIG. 6 is a plan view of an end portion of a light guide assembly in accordance with the features of the present invention.

The problems and disadvantages of the prior art light guide assembly as described hereinabove have been overcome by the light guide assembly having the features of the present invention and as shown in FIG. 6. The light guide assembly in accordance with the present invention includes a light guide in the form of a light tube 155 that is encased by a housing 156 up to the end cap area. It is preferred that the light tubes employed are commercially available liquid light tubes. Installed on the end of the light tube 155 is quartz end member 157. The purpose of the quartz end member is to provide a wear-resistant component relative to the bath water which is not biodegradable and which has excellent optical characteristics. The quartz member provides all such advantages. It was recognized and appreciated by the present invention that placement of quartz member 157 relative to the end cap (and cuvette) was critical to the accuracy of the clinical analyzer which employed such a light guide on its optical guides (e.g. light guides 92 and 94 of FIG. 4).

The light guide assembly shown in FIG. 6 places the cuvette end of the quartz member up against the back side of the wear plate 158 of the end cap and thereby provides an aperture 159 having a depth that is kept between 0.002 and 0.007 inches; which distance is critical to the present invention. By placing the end of the quartz member close to the inside of the end cap, the path of light through the bath water is precisely limited to the depth of the aperture, i.e. 0.002 to 0.007 inches. By maintaining this critical aperture depth in the light guide assembly during the analysis process, a dramatic improvement in the accuracy of the photospectrometer test results is achieved from analysis machine to analysis machine. This is provided by a combination of the accurate control of the size of the aperture depth in the light guide end cap and the resulting short length of bath water that the light path must pass through between the cuvette wall and quartz member 157.

Figure 7:
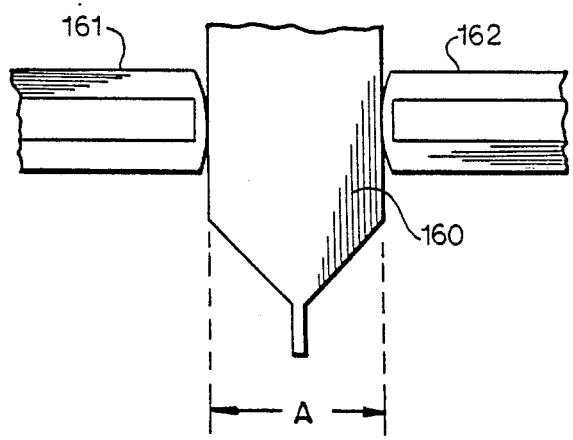
FIG. 7 is a plan view illustrating the positioning of a cuvette between two light guide end caps.

As shown in FIG. 7, during the analysis process cuvettes 160 pass through a channel formed by two light guide end caps 161 and 162 (each of which incorporate the features of the present invention) when the fluid in the cuvette is read by the photospectrometer. Cuvette walls are generally formed in a convex manner (outwardly shaped). To remove any space between the end caps 161 and 162 and each cuvette 160, and insure improved length control (thereby preventing interference with the accuracy of the readings by the photospectrometer) the cuvette walls are made parallel to each other by the end caps. This arrangement enables the cuvette walls to be aligned horizontally by the light guide end caps and vertically by the index holes (item 26 of FIG. 3) in the cuvette belt during analysis. In accordance with the preferred features of the present invention in order to provide a high level of accuracy with regard to the analysis results, the distance A between the light guide and caps 161 and 162 during analysis should be preferably maintained at about 0.195 inches +0.001 to keep the cuvette walls substantially flat and thereby improve the accuracy of the analysis.

By employing such a precise geometric arrangement of the cuvettes between the light guide end caps in accordance with the critical features of the present invention, all of photospectrometers act as one photospectrometer Furthermore, by shortening the depth of the light guide end cap and therefore the amount (distance) of bath water that the light passes through in accordance with the critical parameters described hereinabove, there is basically no chance that bubbles or debris will be present or get trapped in the aperture. Providing the critical geometric structure to the light guide end cap in accordance with the present invention would provide for each analyzer in a clinical analysis system as described hereinabove to be so focused automatically with regard to the light signal thereby substantially eliminating tracking error from analyzer to analyzer.

It should be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. In an automated instrument system for analyzing the constituents of a specimen sample wherein the sample is contained in a cuvette and light is directed to the sample, into a light guide and to a photo-optical system for analyzing the sample, an improved light guide assembly comprising a light guide having projecting at one end portion thereof a quartz member and a housing for containing the end portion of the light guide and the quartz member said housing projecting beyond the end of the quartz member forming an aperture between the quartz member and the housing, the aperture having a depth of between about 0.002 and 0.007 inches.

2. The system of claim 1 wherein said end portion of said light guide assembly and cuvette are disposed in a water bath for maintaining said sample at a predetermined temperature.

3. The system of claim 1 wherein said analysis system includes a plurality of analysis stations each employing said improved light guide assembly.

4. The system of claim 3 wherein said photo-optical system comprises a single light source for generating selected wavelengths of light and separate light guides for transmitting said wavelengths to each of said analysis stations.

5. The system of claim 1 wherein said light guide is a fluid filled light pipe.

6. The system of claim 1 wherein said cuvette is positioned between the end portions of two of said improved light guide assemblies during said analyzing process.

7. The system of claim 6 wherein the walls of said cuvette are made substantially parallel by said end portions when said cuvette is positioned between said light guide assemblies during analysis of said sample.

8. The system of claim 1 wherein the distance between adjacent end portions of said light guide assemblies is about 0.195±0.001 inches.

9. The system of claim 1 wherein said sample is a liquid.

10. The system of claim 1 wherein the said photo-optical system includes a spectrometer.

11. A light guide assembly for directing wavelengths of light comprising a light guide having projecting at one end portion thereof a quartz member and a housing for containing the end portion of the light guide and the quartz member, said housing projecting beyond the end of said quartz member, thereby forming an aperture between the quartz member and the housing, the aperture having a depth of between about 0.002 and 0.007 inches.

12. The assembly of claim 11 disposed in a water bath.

13. The assembly of claim 11 wherein said light guide is a fluid filled light pipe.

* * * * *

UNITED STATES PATENT AND TRADEMARK OFFICE
CERTIFICATE OF CORRECTION

PATENT NO. : 4,801,187

DATED : January 31, 1989

INVENTOR(S) : Lawrence E. Elbert, John C. Mazza, Raymond L. Hecker

It is certified that error appears in the above-identified patent and that said Letters Patent is hereby corrected as shown below:

In column 1, line 9, after "to", delete "to" and insert --a--.

In column 1, line 9, delete "photospectormeter" and insert --photospectrometer--.

In column 1, line 22, delete "simulataneously" and insert --simultaneously--.

In column 1, line 36, delete "throughout" and insert --throughput--.

In column 1, line50, insert --a-- after "in".

In column 1, line 59, delete "4,528,157" and insert --4,523,159--.

In column 1, line 64, delete "4,528,159" and insert --4,477,190--.

In column 2, line 10, delete "hanbling" and insert --handling--.

In column 2, line 28, delete "tracing" and insert --tracking--.

In column 2, line 36, delete "disclsed" and insert --disclosed--.

In column 3, line29, delete "partical" and insert --partial--.

In column 3, line 54, delete "Health Care" and insert --Healthcare--

In column 4, line 31, delete "throug" and insert --through--.

In column 4, line 42, delete "20" and insert --10--.

In column 5, line 29, delete "angler" and insert --sampler--.

In column 5, line 36, delete "848,821" and insert --848,351--.

In column 7, line 25, delete "descreasing" and insert --decreasing--

UNITED STATES PATENT AND TRADEMARK OFFICE
CERTIFICATE OF CORRECTION

PATENT NO. : 4,801,187
DATED : January 31, 1989
INVENTOR(S) : Lawrence E. Elbert et al It is certified that error appears in the above-identified patent and that said Letters Patent is hereby corrected as shown below:

In column 8, line 17, delete "+" and insert -- $\pm$ --.

Signed and Sealed this

Fourth Day of July, 1989

Attest:

DONALD J. QUIGG

*Attesting Officer*    Commissioner of Patents and Trademarks